United States Patent [19]

McCormack

[11] Patent Number: 5,566,877
[45] Date of Patent: Oct. 22, 1996

[54] METHOD FOR INSPECTING A SEMICONDUCTOR DEVICE

[75] Inventor: Dave W. McCormack, Austin, Tex.

[73] Assignee: Motorola Inc., Schaumburg, Ill.

[21] Appl. No.: 432,356

[22] Filed: May 1, 1995

[51] Int. Cl.⁶ .................................................. G01B 11/00
[52] U.S. Cl. ........................... 228/105; 348/126; 348/130
[58] Field of Search ................................... 228/105, 103; 348/129, 130, 126

[56] References Cited

U.S. PATENT DOCUMENTS

| | | | |
|---|---|---|---|
| 4,389,669 | 6/1983 | Epstein et al. | 358/101 |
| 4,872,052 | 10/1989 | Liudzius et al. | 358/106 |
| 4,891,767 | 1/1990 | Rzasa et al. | 395/94 |
| 5,060,389 | 10/1991 | Frederick | 33/1 BB |
| 5,138,180 | 8/1992 | Yamanaka | 250/561 |
| 5,156,319 | 10/1992 | Shibasaka et al. | 228/9 |
| 5,170,062 | 12/1992 | Miyahara | 250/561 |
| 5,353,356 | 10/1994 | Waugh et al. | 348/130 X |

Primary Examiner—Kenneth J. Ramsey
Attorney, Agent, or Firm—Patricia S. Goddard

[57] ABSTRACT

A method for inspecting a semiconductor device includes an inspection station (10), a handling system (12), a microscope (14), a camera (18), and a computer (20) having a monitor (22). A magnified image (40) of the device being inspected is transmitted to monitor (22) via camera (18). A template image (60) is then recalled from computer readable memory and is superimposed upon the magnified image of the device appearing on monitor (22). The template image (60) includes transparent regions (62) and opaque regions (64). The opaque regions block out all areas of the device not associated with the characteristic being inspected, while the transparent regions highlight the area of interest. Using the superimposed image (70), the operator can quickly focus on the area of the device requiring attention. In specific embodiments of the invention, a template is used to assist inspection of a wire bond configuration, a die attach material bondline, lead skew, and mark placement.

22 Claims, 11 Drawing Sheets

METHOD FOR INSPECTING A SEMICONDUCTOR DEVICE

FIELD OF THE INVENTION

The present invention relates to inspection methods, and more particularly to methods for inspecting semiconductor devices.

BACKGROUND OF THE INVENTION

Inspection operations are imposed throughout manufacturing processes to insure that the product being produced conforms to the manufacturer's quality standards. Semiconductor manufacturing is no exception. Inspection for defects, for alignment tolerances, and for critical dimension control are just a few of the characteristics of a semiconductor device which are inspected during wafer fabrication processes. Once wafer fabrication is complete, the wafer moves to assembly operations for packaging. Within assembly, inspections occur to insure, for example, that a semiconductor die is aligned properly within a package, that the appropriate number of wire bonds or solder bumps are formed on a device, and that the package leads are coplanar.

During each of these inspection processes, an operator is charged with comparing the device being inspected to a standard which has been approved as an acceptable level of quality. The accepted standard can take many forms, but is very often simply a piece of paper noting in words or with a drawing what an acceptable product should look like. While such "paper standards" have the advantage of simplicity, use of paper standards also impose a high degree of human error.

One example of a paper standard which is sometimes used by semiconductor manufacturers is the use of a paper wire bond diagram to inspect the configuration of wire bonds of a semiconductor device. Some semiconductor devices are designed such that not all bond pads of a die are wire bonded to a corresponding lead, or more commonly that not all lead of a designed package are wire bonded to a die bond pad. In order for an operator to understand which bond pads and which lead are to include wire bonds, a diagram is created on paper to indicate where wire bonds should be located. To inspect an actual wire bonded device, an inspector views the device through a microscope and compares the image as magnified by the microscope optics to the paper wire bond diagram. Having to repeatedly view the image of the device under the microscope and turn away to view the paper wire bond diagram creates a number of opportunities for error. For instance, operators can lose their place in making a comparison, creating the potential for portions of the device to pass without inspection. Furthermore, the repeated motion of viewing a microscope image and then viewing a paper image increases cycle time and reduces throughput during the inspection process. Also, because the paper wire bond diagram only marginally presents the actual image as seen under the microscope, use of a paper diagram tends to make the inspection process tedious, time consuming, confusing, and susceptible to error.

With the emergence of highly advanced manufacturing and inspection equipment, some inspection operations have the potential for being fully automated. By incorporating optical recognition capability and integrated software, some semiconductor manufacturing and inspection equipment is available which does an electronic comparison between the device being inspected and a stored electronic file containing information about a manufacturer's acceptable standards. For example, a digitized version of the device being inspected is generated and is compared to a digitized version of an accepted standard. The comparison of the two digitized files is performed by a computer, and the results of the comparison provide an "accepted" or "rejected" output. In an ideal world, such a sophisticated digital comparison would seem to be the perfect solution. However, in a manufacturing world, such a solution is sometimes not possible. The sophisticated equipment necessary to perform such automated inspections is very expensive. Moreover, the time it takes for the equipment to do the comparison and to provide a result only inhibits a manufacturer's goal of reducing total cycle time. Furthermore, the systems are not usually entirely automatic. Some human intervention is still needed, for example to make close judgement calls.

Therefore, a need exists for an improved inspection process for semiconductor devices wherein an inspection can be accomplished in a very quick, efficient manner, with much smaller room for error as compared to prior art paper standard techniques. Moreover, it is desirable for such an inspection method to be practiced with minimal capital investment.

DETAILED DESCRIPTION OF A PREFERRED EMBODIMENT

Figure 1:
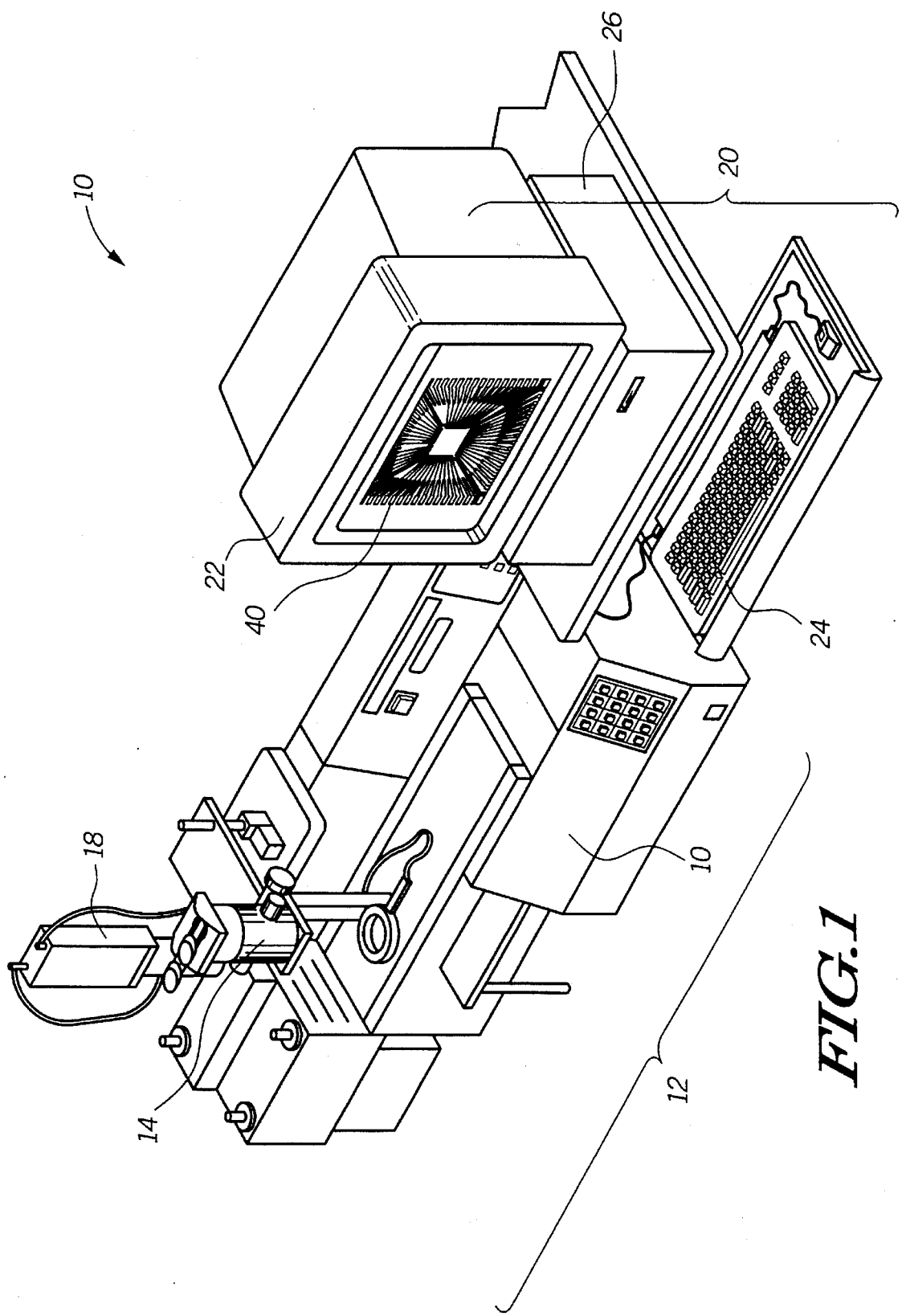
FIG. 1 is a perspective view of an inspection system suitable for practicing the present invention.

The present invention provides a fast, inexpensive method of inspecting semiconductor devices at various stages throughout the manufacturing process, and particularly throughout the assembly process. While the present invention does not remove all possibility of error during the inspection process, the possibility of human error is significantly reduced as compared to prior art inspection methods which rely upon standards set upon paper. The present invention provides a nice compromise between the error prone inspection methods which rely upon operator judgment and those which are fully automated as a result of technological improvements in the inspection equipment, but which are expensive and require too much time to complete an inspection. Generally, a method of inspecting in accordance with the present invention involves positioning the device to be inspected under a microscope, and transmitting a magnified image of the device from the microscope to a computer monitor via a camera. A template which has been specifically created for the device characteristic which is being inspected is retrieved from computer memory or computer readable, memory and is displayed on the computer monitor, superimposed on the magnified device image already present on the monitor. An inspection station operator then compares the device being inspected as shown on the monitor with the template and determines whether the device falls within the accepted standards set by the manufacturer and as accounted for in the template. If the device being inspected conforms with the template, the device is accepted, otherwise the device is rejected.

In more specific embodiments of the present invention, the characteristic being inspected is either a wire bond configuration, the location of a die attach material bondline, or lead and marking positions. In using the present invention to inspect a wire bond configuration, a template is created to have opaque portions and transparent portions. Opaque portions of the template are designed to block out all portions of the device being inspected except for the actual wire bonds. The transparent portions thus correspond to where actual wire bonds are supposed to be located. Upon superimposing the template on to the magnified image of the device being inspected, only the wire bonds will be visible on the computer monitor. Thus, the image which an inspection station operator looks at during an inspection is focused only where the operator needs to look to properly inspect the device. Extraneous portions of the magnified image are blocked out by the opaque regions of the template. Similarly, in using the present invention to inspect a die attach material bondline, a template is created to have opaque portions which block out portions of the magnified image other than the die attach bondline. Moreover, the template is designed to define a lower limit or an upper limit (or both) as to where the die attach material bondline can acceptably exist along the die side. Likewise, a template can be used to inspect external leads position in a packaged device. In the template, transparent portions highlight the leads tips and define acceptable limits on lead tip positions. A manufacturer's product marking position can also be inspected using templates. By employing a simple template with opaque and transparent regions superimposed upon a magnified image of the device being inspected, the present invention focuses an inspector's attention to that characteristic being inspected and facilitates a quick "pass" or "reject" ("go" or "no go") result for the inspection process.

These and other features, and advantages, will be more clearly understood from the following detailed description taken in conjunction with the accompanying drawings. It is important to point out that the illustrations are not necessarily drawn to scale and that there can be other embodiments of the present invention which are not specifically illustrated. Throughout this description and in the figures, like reference numerals are sometimes used to designate identical or corresponding parts.

Figure 2:
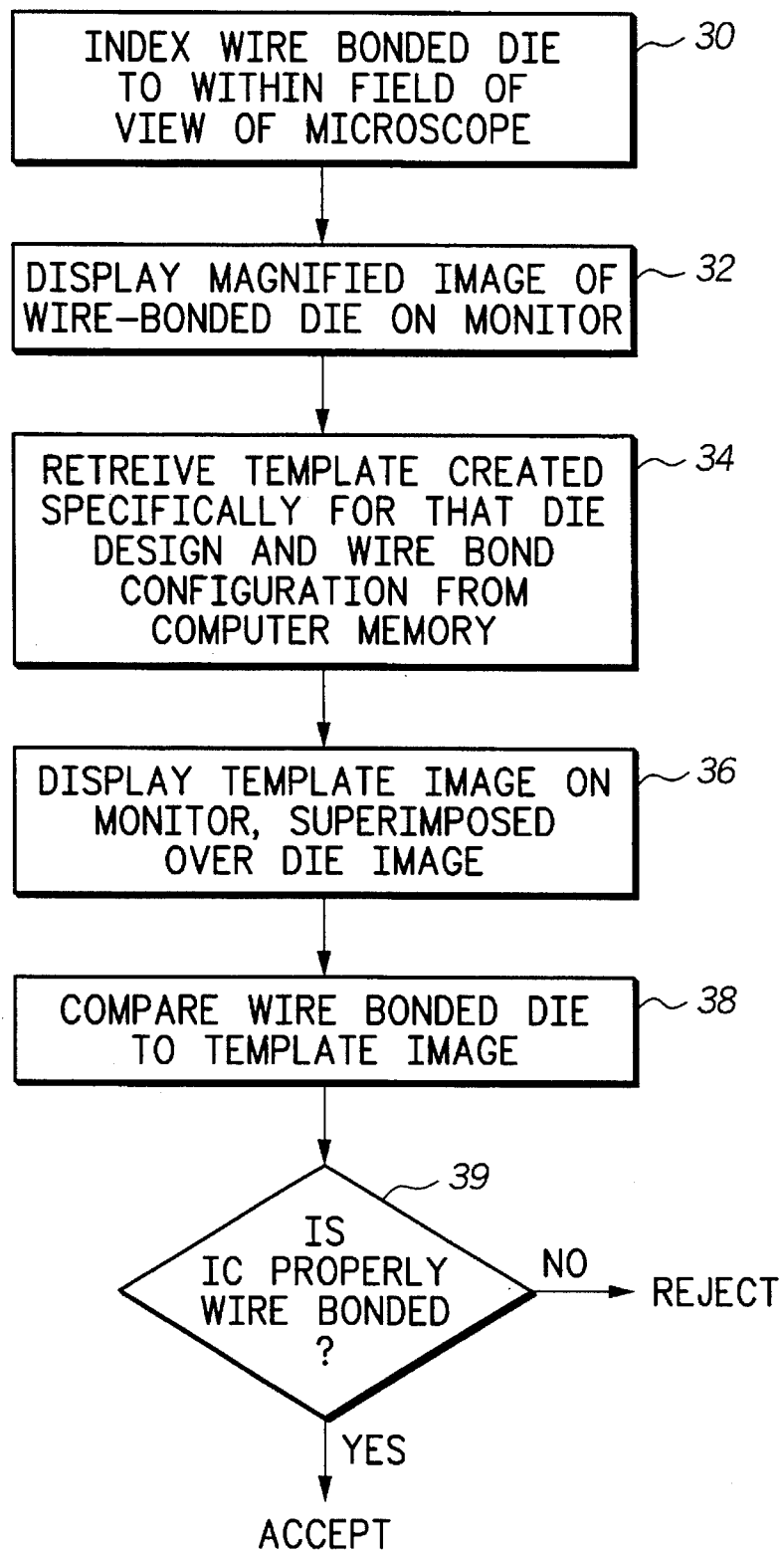
FIG. 2 is a flow chart which includes inspection steps in accordance with one embodiment of the present invention.

FIG. 1 illustrates an inspection station 10 which is suitable for practicing the present invention. Inspection station 10 includes a handling system 12, a microscope 14, a camera 18, and a computer 20. Computer 20 includes a monitor 22, a keyboard 24, and a controller unit 26 with memory. FIG. 2 is a process flow chart indicating the most important steps for carrying out an inspection process using the present invention.

In operation, a semiconductor device or multiple devices are loaded into handling system 12, for example by inserting a cassette or magazine filled with a plurality of devices at the front end or entrance of the handling system. Handling system 12 is used to unload one device from the magazine and convey or index it to within a stage area in a field of view of microscope 14, as indicated by a step 30 in FIG. 2. In a conventional inspection process, an operator would view the device being inspected through the optics of the microscope. In accordance with the present invention, instead a magnified image 40 of the device being inspected is transmitted to monitor 22 by camera 18. Displaying the magnified image on monitor 22 is a step 32 of the: process flow of FIG. 2. As illustrated and described in reference to FIGS. 1–5, the characteristic being inspected is a wire bond configuration of a semiconductor device. Accordingly, the magnified image appearing on monitor 22 is that of a semiconductor die as it is wire bonded to a plurality of leads.

Figure 3:
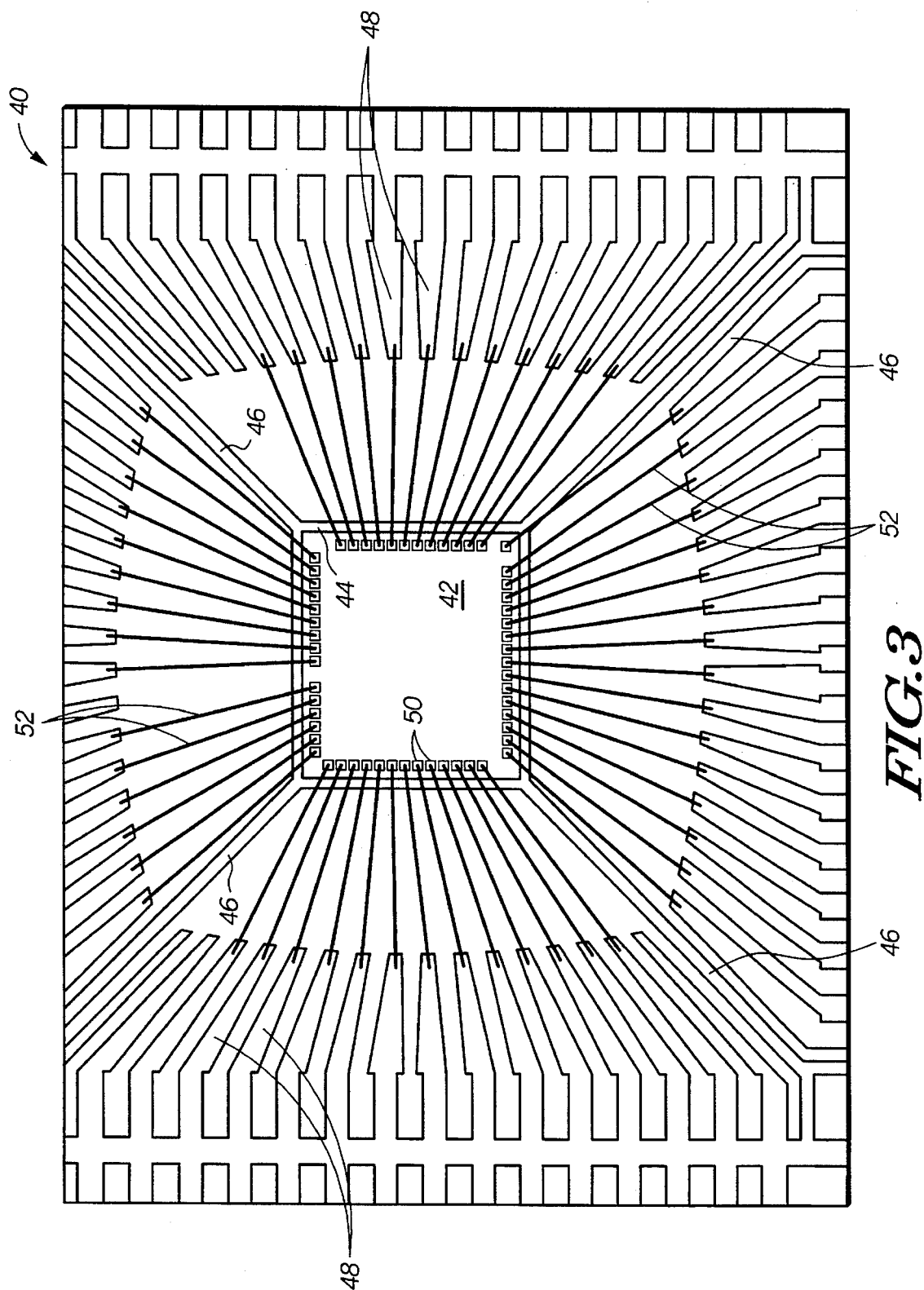
FIG. 3 is a magnified image of a top view of a wire bonded semiconductor die as it would appear through a microscope and as displayed on a monitor/in accordance with the present invention.

Magnified image 40 as it appears on monitor 22 is illustrated in more detail in FIG. 3. Elements of the magnified image include a semiconductor die 42 (for example, an integrated circuit) which is mounted to a die paddle or die flag 44 of a lead frame. Also included as part of the lead frame are tie bars 46 which support the die flag, and a plurality of leads 48. Semiconductor die 42 includes a plurality of bond pads 50 which are electrically coupled to the plurality of leads by a plurality of wire bonds 52. Wire bonds 52 are wire bonded between bond pads 50 and leads 48 in accordance with conventional methods. During a wire bond configuration inspection, it is necessary to determine whether wire bonds 52 are wire bonded to the appropriate leads and the appropriate bond pads. In many instances, not all leads or not all bond pads of the die are designed to be used. Accordingly, during the inspection an operator will see that some leads do not have wire bonds connected to them. However, this may be by design. For an operator to determine which leads need to be bonded, and to which bond pads, in the past the operator referred to a paper wire bonding diagram. But in comparing the device being inspected to a wire bond diagram, there was large room for human operator error and confusion. The present invention simplifies the inspection process by eliminating the need for paper wire bonding diagrams, or other paper standards, and instead employs a template.

In displaying the magnified image onto the monitor, it is preferred that the entire area to be inspected is within the field of view of the micrope, and is thus displayed on the monitor, as illustrated in FIG. 3. Once magnified image 40 is displayed on monitor 22, the inspection station operator calls up from the computer memory a template specifically created for the characteristic being inspected, as indicated in a step 34 of FIG. 2. Upon retrieving the template in electronic form, the template is also displayed on monitor 22, superimposed onto magnified image 40, as recited in a step 36 of the process flow of FIG. 2. The template can be called up from memory using keyboard 24, and can preferably be accomplished by pressing a single key on the keyboard. Existing software programs to simplify the key stroke combination necessary to retrieve files or perform other computer functions can be used to facilitate recall and display steps.

Figure 4:
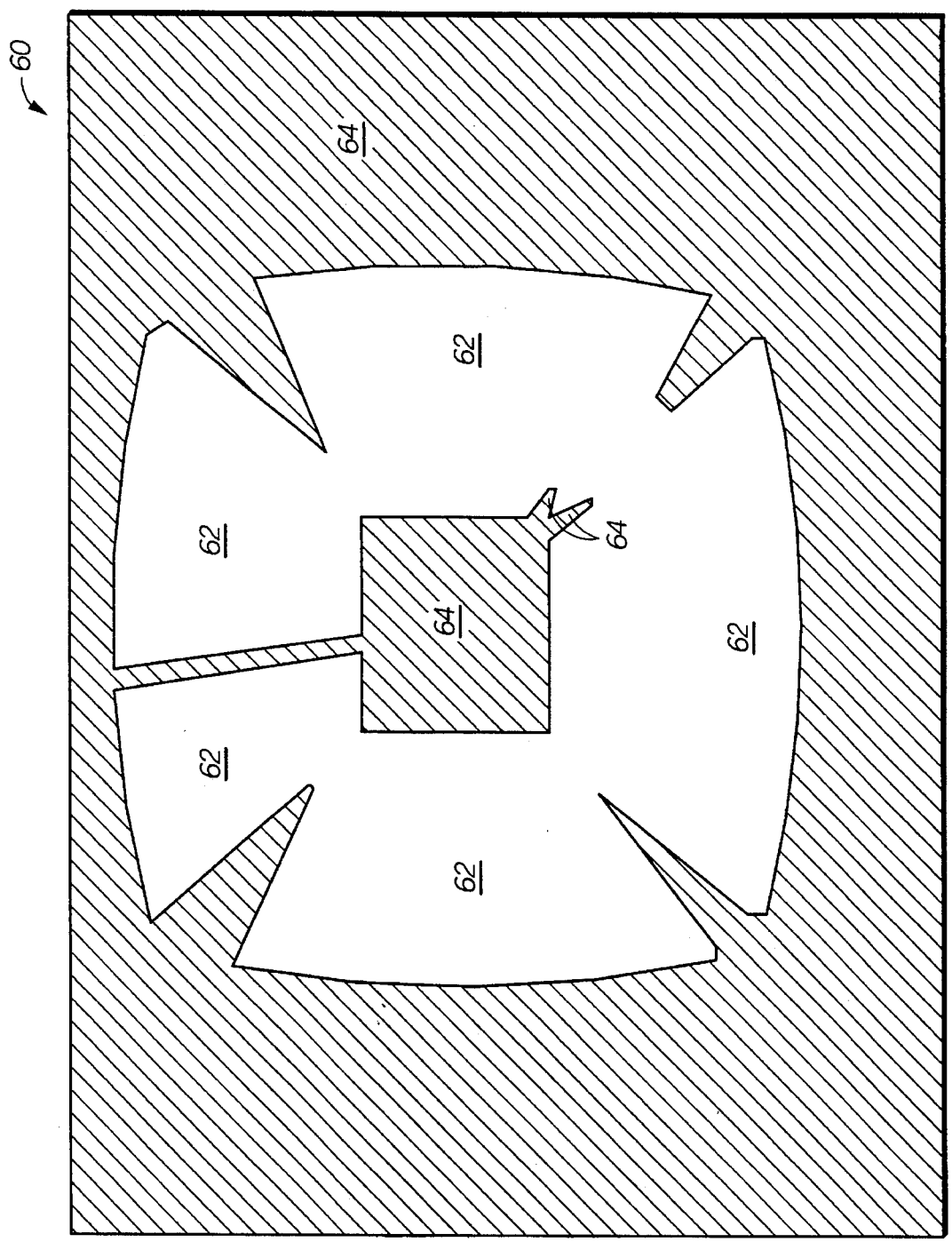
FIG. 4 is an image of a template having transparent and opaque portions defining proper wire bonded areas of the semiconductor die illustrated in FIG. 3, and as it would appear by itself on a monitor in accordance with the present invention.
Figure 5:
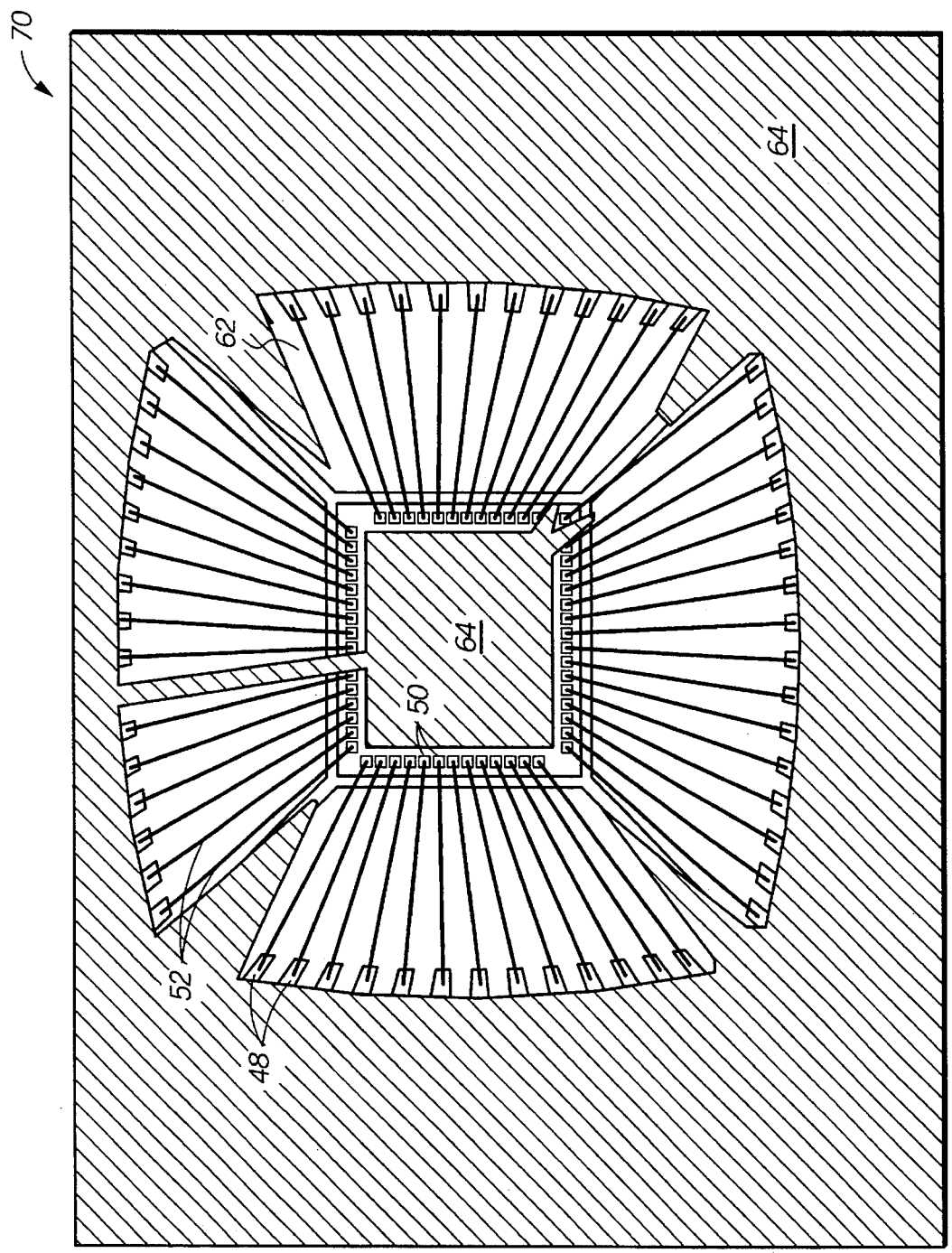
FIG. 5 is an image of the template illustrated in FIG. 4 superimposed onto the magnified image of the wire bonded semiconductor die illustrated in FIG. 3, and as displayed on a monitor in accordance with the present invention.

FIG. 4 is a template image 60 of a template designed for inspecting a wire bond configuration for die 42 as it would appear (by itself) on monitor 22 upon being retrieved from memory. Template image 60 is one of numerous template designs which could be used in accordance with the invention. The actual template design will depend upon the particular device characteristic being inspected. Generally, template image 60, and other templates used in accordance with the invention, have two primary components; transparent regions 62, and opaque regions 64. Although opaque regions 64 (and others illustrated herein) are shown as being cross-hatched to meet drawing requirements, preferably the regions are solid in color, for example black, to enhance the contrast between the opaque regions and transparent regions. Opaque regions 64 are designed to hide all portions of the magnified image of the wire bonded device except those regions including wire bonds. Thus, transparent regions 62 highlight only the wire bonded portions of the device. Upon retrieving the template from the computer memory and displaying the template image 60 on monitor 22, the image of the template is superimposed upon the already existing magnified image 40 of the wire bonded device, to create a superimposed image 70 as illustrated in FIG. 5.

Once superimposed image 70 is established on monitor 22, the operator in charge of the inspection station compares the magnified image of the device and the image of the template, as indicated in a step 38 of the process flow of FIG. 2. The result of the comparison step leads to a conclusion as to whether the device being inspected is acceptable or should be rejected, as indicated by a decision step 39 in FIG. 2. As can be seen by FIG. 5, superimposed image 70 provides a very clear image for an inspection station operator to view in inspecting for a proper wire bond configuration. Wire bonded regions of the device being inspected are visible through transparent regions 62 of the template, while other regions of the device being inspected are blocked out by opaque regions 64. Thus, the inspectors attention is focused only on that characteristic of the device being inspected, in this case the wire bond configuration. There is no point during the inspection process where the examiner has to look away from the device being inspected, for example to look at a paper wire bond diagram. Thus, the likelihood of the operator losing his or her place during the inspection is significantly reduced. As can be seen by the superimposed image 70 shown in FIG. 5, the template can be designed to hide those leads which are not to include a wire bond by making those regions of the template image opaque. Accordingly, an operator can tell in an instant whether or not the appropriate leads are wire bonded, and thus render a decision as to whether the device should be accepted or rejected.

It is noted that in some instances a wire bond may exist from die 42 to a lead 48, but that the wire bond is not supposed to be there, in which case it may be covered by an opaque region of the template. Looking only at the superimposed image 70, this wire bond would be hidden, and not visible to the inspector. However, the computer system can be configured so that an operator can toggle back and forth between viewing only an image of the device being inspected and the superimposed image which includes both the device being inspected with an overlaying template image. The operator can then look for the existence of wire bonds beneath otherwise opaque regions of the template to reject the device as being improperly wire bonded.

Figure 6:
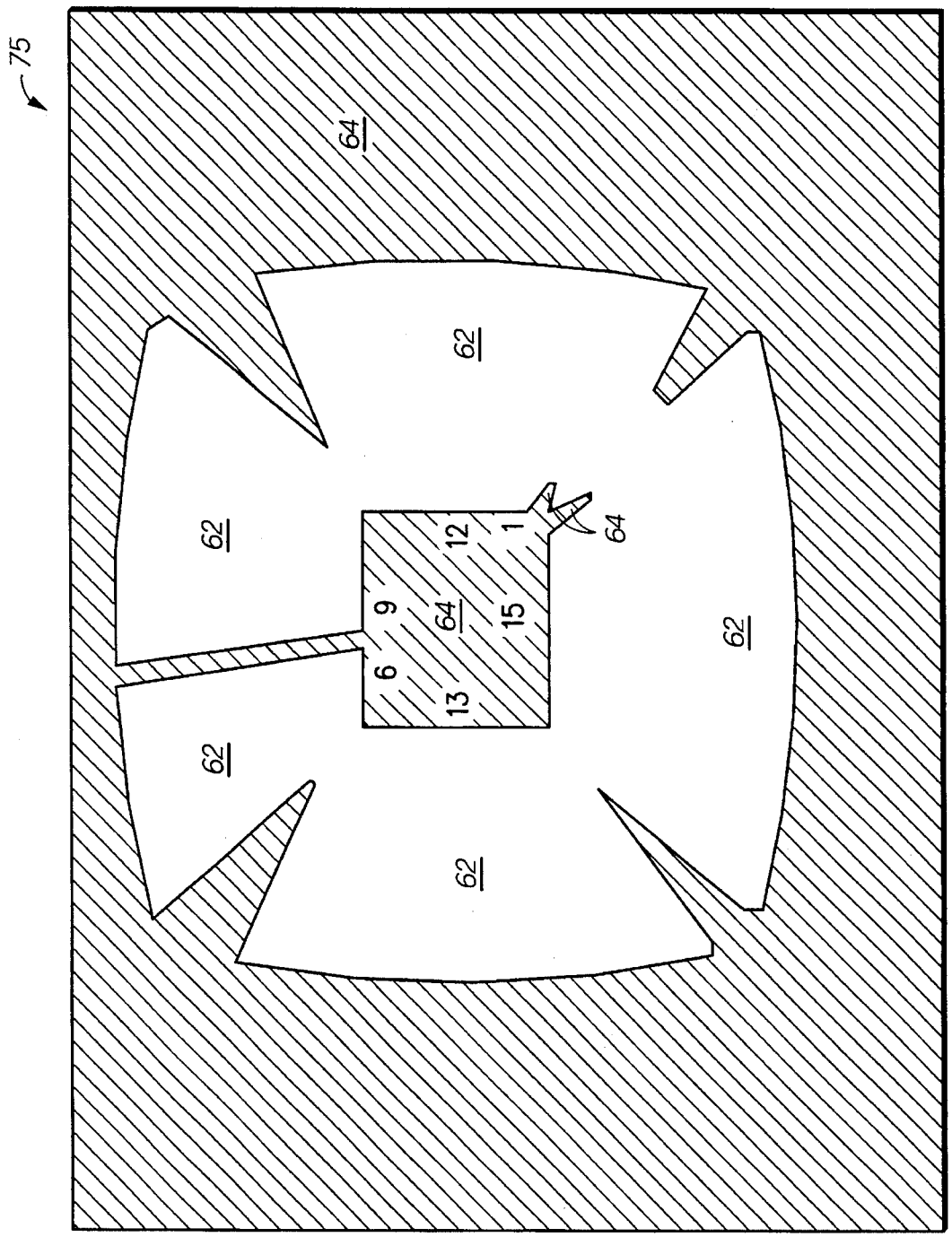
FIG. 6 is another image of a template, like that illustrated in FIG. 4, but with the enhancement of alpha-numeric characters (in this case numbers) to facilitate the inspection process.

Enhancements can be made to template image 60 to further facilitate the inspection process. For example, in reference to using a template to inspect a wire bond configuration, alpha-numeric characters or symbols can be added to the template such as shown in FIG. 6. FIG. 6 illustrates a template image 75 much like the template image illustrated in FIGS. 4 and 5 but which include a series of numbers corresponding to transparent sections of the template image. The numbers listed next to each transparent section correspond to the number of wire bonds which should be included within that region. For example: along the left edge of the die there should be thirteen wire bonds; along the bottom side of the die there should be fifteen wire bonds; at the bottom right corner there should be one isolated wire bond; along the right side of the die there should be twelve wire bonds; and along the top edge of the die, there should be two segments, one with nine wire bonds and the other with eight wire bonds, with an unbonded lead separating these two sections. In addition to the wire bond count, alpha-numeric characters can be included to denote non-standard bonding arrangements. For example, the locations of double bonds, wherein two wires are connected to one lead, can be denoted by "Double" or "2W". Similarly, "G" or "GND" can be used to denote that a wire is connected to a ground. Caution is advised, however, to avoid overcrowding the template image with alpha-numeric symbols. The image that the operator must view during inspection should be relatively clear and unobstructed for inspecting the characteristic at hand.

Figure 7:
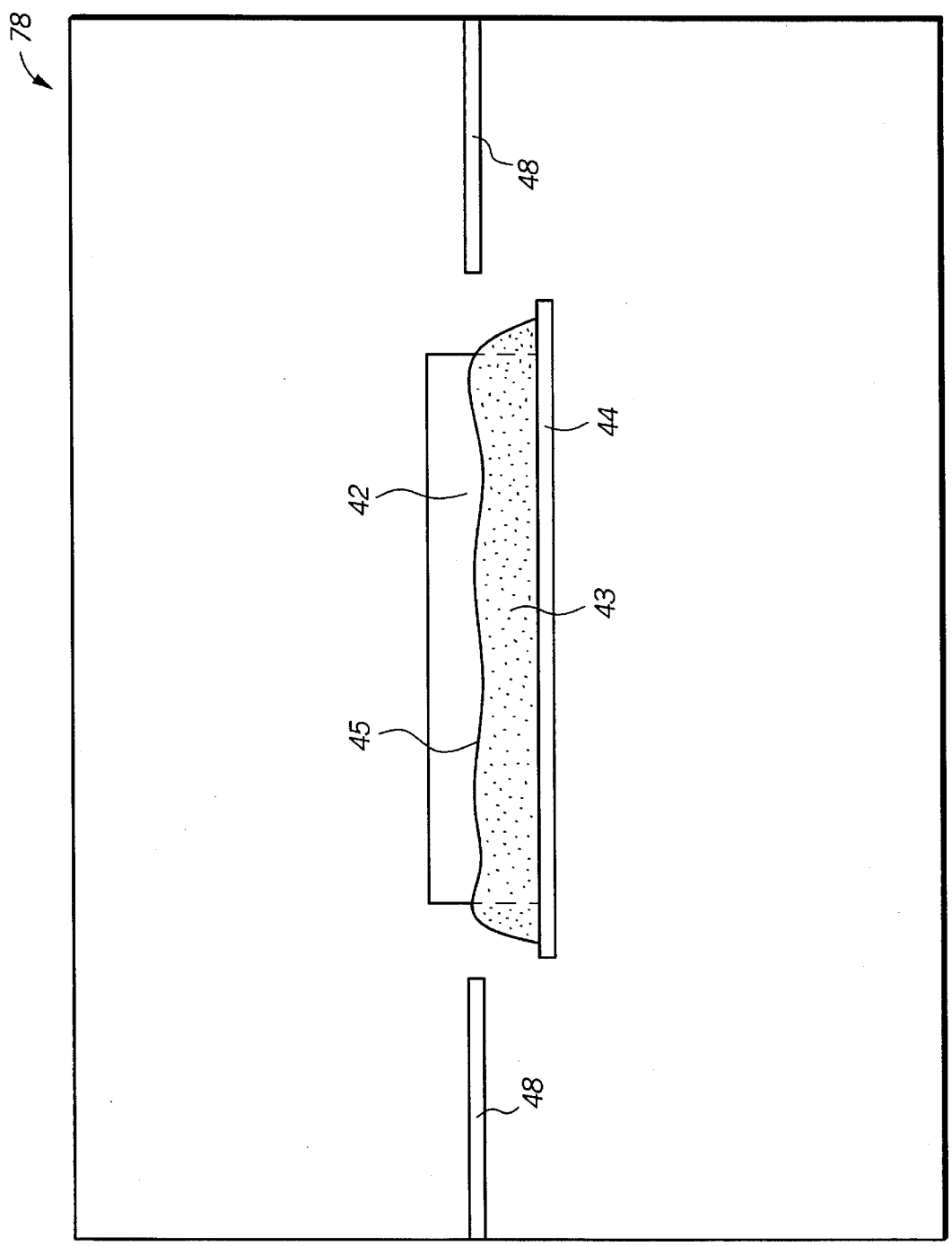
FIG. 7 is a magnified image of a side view of a semiconductor die mounted to a lead frame flag using a die attach material as it would appear through a microscope and as displayed on a monitor in accordance with another embodiment of the present invention.

FIG. 7 illustrates an example of using the present invention for inspecting a die attached material bondline. Shown in FIG. 7 is a magnified image 78 of a side view of semiconductor die 42 as it is mounted on flag 44, and prior to being wire bonded to leads 48. The die is attached to flag 44 using a conventional die attach material 43, which for example is a silver-filled epoxy. The die attach material creates a bondline 45 along each of four sides of the die. The location of the bondline (how far up along the die edge or side face the die attached material exists) is important, and is usually inspected. Having the bondline too close to the flag (i.e. not high enough up the die side) results in an unreliable die attachment, while having the bondline too close to the active surface of the die creates a potential problem of electrically short circuiting the device since the die attach material is usually electrically conductive. Accordingly, semiconductor manufacturers set an acceptable range within which the bondline can exist. Looking only at a side view of the die on the flag makes it difficult for an operator to determine if the bondline is appropriately within the accepted range. However, with the help of the present invention, this range can easily be incorporated into a template which is overlaid or superimposed upon the magnified side view of the die, allowing the operator to give a quick "pass" or "fail" conclusion as to whether the bondline falls within an accepted range.

Figure 8:
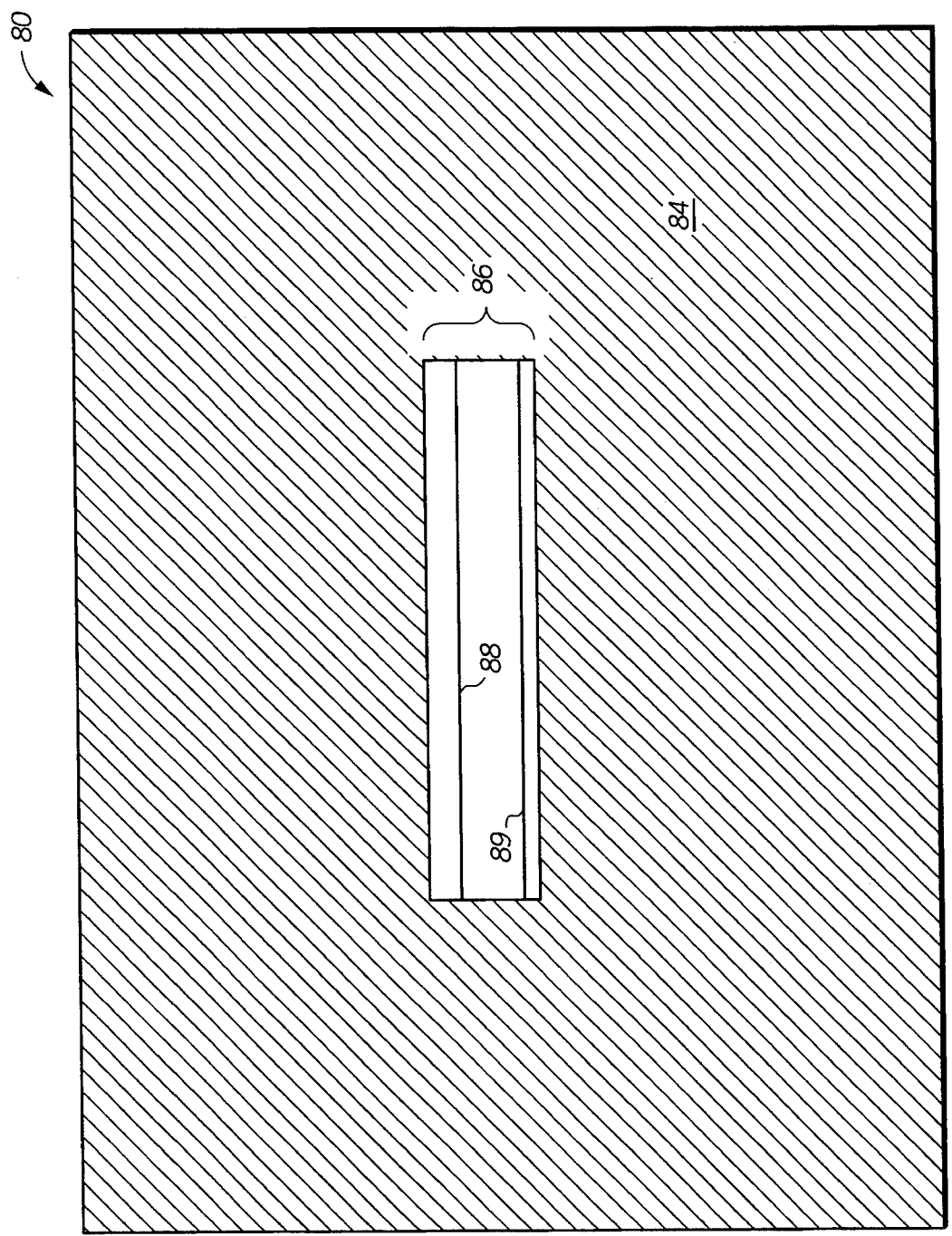
FIG. 8 is a image of a template having a transparent rectangle which corresponds to the side of the semiconductor die illustrated in FIG. 7 and includes an upper limit line for inspecting a bondline of the die attach material.

An example of what one suitable template for inspecting a die attach material bondline looks like is illustrated in FIG. 8. A template image 80 has an opaque region 84 and a transparent rectangle 86. Again, opaque region 84 is preferably solid in color rather than cross-hatched as shown.

Figure 9:
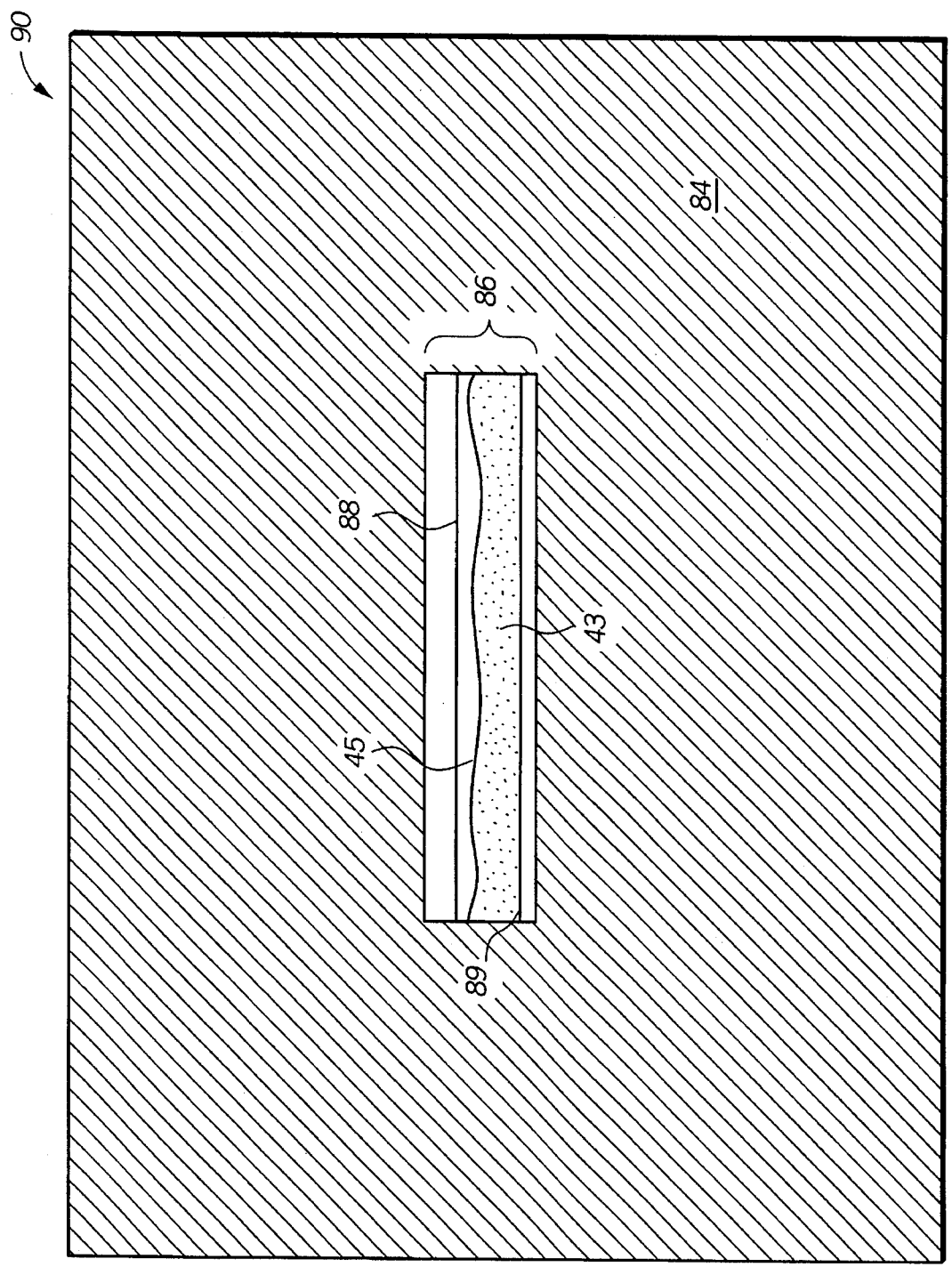
FIG. 9 is an image of the template illustrated in FIG. 8 superimposed onto the magnified image of the side view of the semiconductor die illustrated in FIG, 7, and as displayed on a monitor in accordance with the present invention.

Rectangle 86 is created to correspond with the top, bottom, and side boundaries of the magnified image of the side view of die 42 shown in FIG. 7. It is noted, however, that the shape of a transparent region used for inspecting a die attach material bondline need not be a reactangle. Other shapes are likely to be suitable as well. Included within rectangle 86 are two opaque lines, specifically an upper limit line 88 and a lower limit line 89, as defined by a manufacturer's acceptable bondline height. As an example, lower limit line 89 can correspond to a distance of 5 percent of the total die height, while upper limit line can correspond to a distance of 75 percent of the total die height. Template image 80 is superimposed onto the magnified image of the side view of the die 42 to create a superimposed image 90, as illustrated in FIG. 9. In superimposed image 90, the magnified image of the device as illustrated in FIG. 7 is visible within transparent rectangle 86 such that the bondline 45 can be viewed by the operator. Because bondline 45 exists below the upper limit line 88 and above lower limit line 89, the inspector can immediately determine that the device passes inspection. If bondline 45 is not present entirely between the two limit lines, the device is rejected. As an alternative to limit lines, the transparent rectangle itself could define the upper and lower limits for the die attach material bondline. For example, the lower edge of the rectangle could serve as the lower limit and the upper edge as the upper limit.

It is noted that in inspecting a die attach material bondline, generally one should inspect more than the bondline location on just one side of the die. Preferably, the bondline of all four sides of the die are inspected. In accordance with the present invention, inspection of all sides can be accomplished quite simply by utilizing four cameras (one for each side). The magnified image being displayed on the monitor can be rotated around the four sides of the device by changing which camera's input signal is being displayed on the monitor, without requiring movement of the device being inspected. Preferably, the cameras are positioned at angles ranging from about 25°–30° from the horizontal plane of lead frame and die flag.

Figure 10:
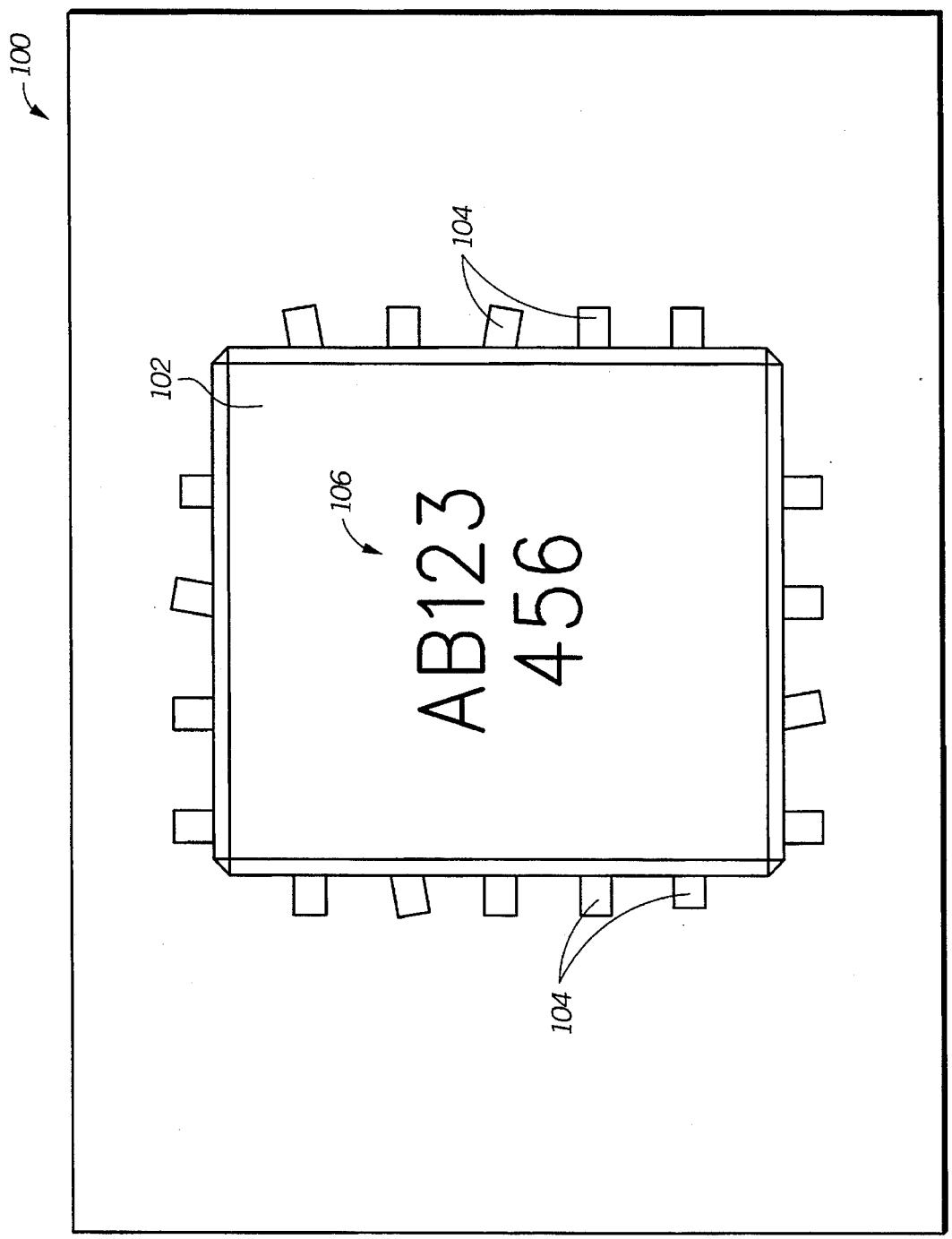
FIG. 10 is a magnified image of a top view of leaded, packaged semiconductor device.

In accordance with yet another embodiment of the present invention, a template is used to inspect geometric tolerances of semiconductor package leads and marks. Illustrated in FIG. 10 is an image 100 of a leaded, packaged semiconductor device from a top view. The device as illustrated is a magnified image as it might appear on a monitor in accordance with the invention. The device includes a package body 102, a plurality of leads 104, and a manufacturer's mark 106. Once the device is encapsulated in package body 102, leads 104 are cut from a strip lead frame and formed into the desired lead configuration (for example, gull-wing, J-lead, or dual-in line). During the cutting and forming operations, and during handling operations, the leads can get moved from their original desired positions. For instance, as illustrated in image 100, some of the leads of the device are skewed (are not perpendicular to the package). Normally, a device's leads are not skewed as severly as illustrated. The exagerated lead positions are shown for demonstrations purposes. Skewed leads are unacceptable because the leads will no longer match the substrate pad configuration to which a user will mount the device. Likewise, leads which are too short will not be able to match a user's pad configuration. An inspection in accordance with the present invention uses a template to determine if the extent of lead skew and overall position is acceptable.

Figure 11:
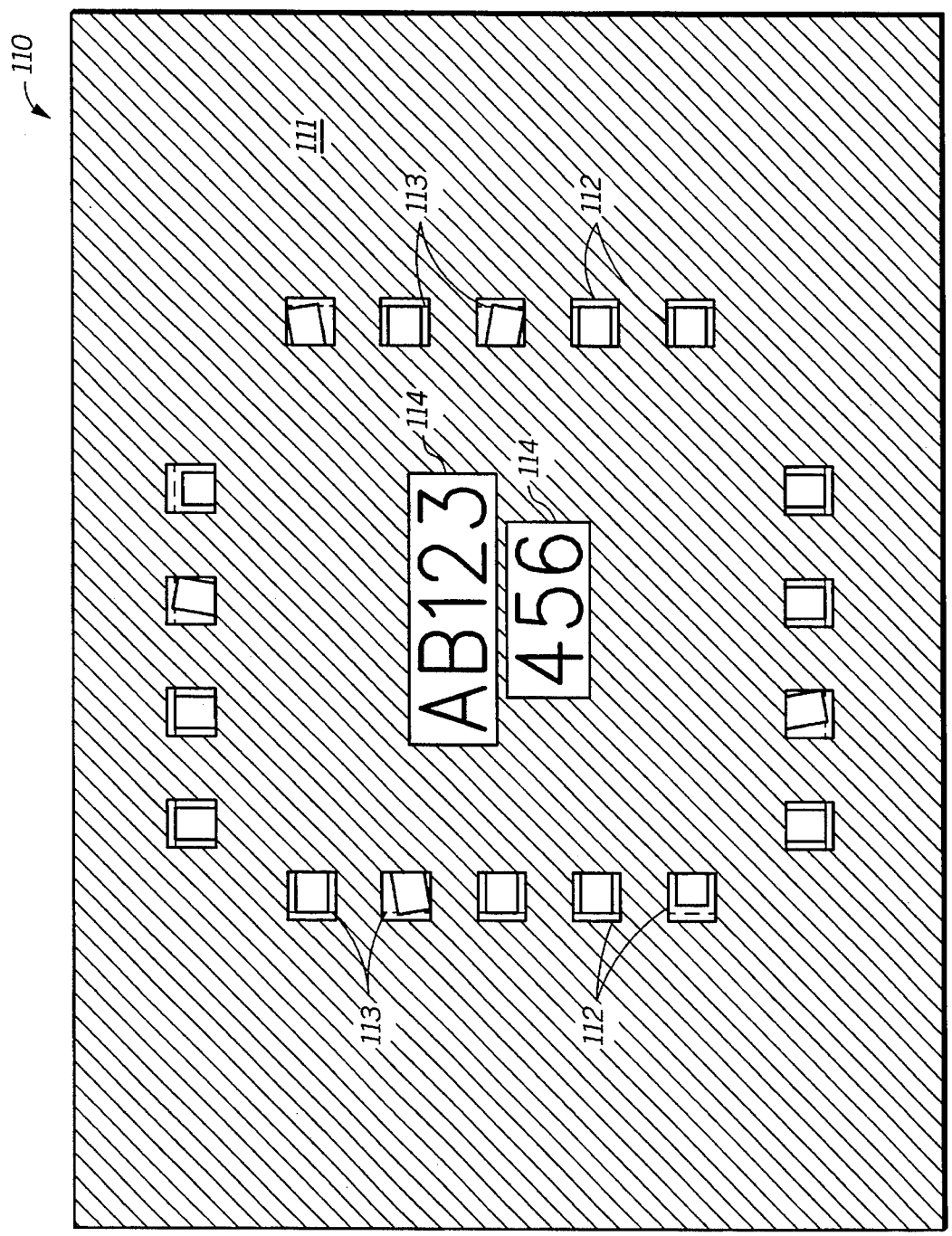
FIG. 11 is an image of a template superimposed onto the magnifed image of the leaded, packaged semiconductor device in FIG. 10, and as displayed on a monitor in accordance with another embodiment of the present invention.

As demonstrated in FIG. 11, a template has opaque portion 111, within which are formed transparent squares 112 corresponding to the acceptable limits of lead location. There is a transparent square associated with each lead of the device. The template is superimposed onto a magnified image of the leaded device, and together the template and magnified image of the device are displayed on a monitor as a superimposed image 110. Within each transparent square 112 is a minimum lead length line 113. Leads lengths and other geometric parameters are often set according to industry standard. Thus, during an inspection process, minimum lead length line 113 can be used to make sure each lead is at least a specified length. An inspector views each transparent square 112 to make sure each lead 104 extends to the minimum lead length line 113. To inspect lead skew, transparent rectangles are designed and dimensioned such that if any portion of the lead touches an edge of the transparent square, the lead is too severly skewed and fails the inspection. As illustrated in FIG. 11, some leads are illustrated as being too skewed and too short to pass inspection, again in an exaggerated manner.

Superimposed image 110 also demonstrates that the present invention can be used to inspect geometric tolerances for a manufacturer's product marking. Most manufacturer's mark their semiconductor devices with a product number, their company logo, and perhaps a manufacturing date code. These manufacturers often have strick compliance guidelines for where on the device the mark can be placed. A template can be created to account for an inspection of the mark placement as well. Superimposed image 110 of FIG. 11 shows two transparent rectangles 114 within opaque portion 111 which correspond to the two lines of alpha-numeric characters constituting a mark 106. It is noted that a mark may include any kind of symbol, rather than just alpha-numeric characters as illustrated, and may be of any size. With a quick look at superimposed image 110, an inspector can instantly tell whether the mark is properly placed.

WORKING EXAMPLE

Now that the present invention has been described in somewhat general terms, a more detailed description of how to actually implement the present invention follows. The following description will include information pertaining to particular equipment and software which was used to establish the present invention, however, the present invention should not in any way be limited to the particular configuration and setup herein described. Alternative equipment and alternative software can be used to accomplish the same objectives and still fall within the scope of the present invention. While the following working example is described in reference to using the present invention to inspect wire bond configurations for semiconductor devices, as noted earlier the present invention is not limited to inspecting this particular device characteristic. Principles, equipment, and software which are used and described in the working example can be extended to a variety of inspections needed throughout the semiconductor wafer fabrication and assembly process.

An inspection station for practicing the present invention was built from, and based upon, an Allteq Series 3000 inspection station, available from Allteq Industries, Fremont, Calif. The Allteq Series 3000 includes both a handling system for moving the devices and a microscope. The microscope on the Allteq Series 3000 did not have a large enough field of field to view the entire wire bonded die and surrounding leads, nor was the microscope believed to have sufficient resolution. Therefore, the microscope which came with the inspection station was replaced with a Leica Wild M3Z microscope. A charge coupled device (CCD) camera was installed on the microscope and connected to enable transmission of the magnified image created by the microscope to a computer monitor. A high resolution CCD camera made by Sony Corporation, Model No. SSC/C374, was found to be suitable for this purpose. A Macintosh Quadra, Model 840AV, a computer made by Apple Computer, Inc. of Cupertino, Calif., was utilized also in the inspection station. The computer was equipped with 24 megabyte of RAM (random access memory), a 230 megabyte hard drive, and had built in video support (1 Meg Video RAM, upgradable to 2 Meg). The monitor used was a 20 inch multi-sync monitor, also made by Apple Computer. An output of the CCD Camera was connected to an input of the computer to enable the magnified image of the device being inspected to be displayed on the monitor. An inspection station such as that described above (including the software described below) can be set up for a cost in the range of only $20,000–$30,000 as compared to fully automated stations which cost in excess of $100,000.

Software which was used to establish the present invention includes Video Monitor Version 1.0 and Simple Text Version 1.1.1, by Apple Computer, Inc., which comes pre-installed on the Quadra 840AV Apple Computer system, Quick Keys Version 3.0 by CE Software, Inc., of West Des Moines, Iowa, File Typer Version 4.1.2 (shareware available from Daniel Azuma of Sunnyvale, Calif.), and Photoshop Version 2.5.1 by Adobe Systems, Inc., of Mountain View, Calif. The Quick Keys software is used to enable an inspection station operator to simply press one key on the keyboard to perform a pre-specified task. For example, Quick Keys was used to create designated key stroke functions called "Video" and "Template." Upon pressing the Video key, a magnified image of the device being inspected as visible through the microscope is displayed upon the computer monitor via the camera. Upon pressing the Template key, the appropriate template for the device being inspected is called from computer memory and displayed on the monitor superimposed onto the magnified image of the device being inspected.

The Photoshop software was utilized to create the templates used in practicing the present invention. To create the templates, features of Photoshop not discussed in the software's user manual (copyrighted 1993) were utilized. Accordingly, a discussion of how to use these features to create the templates is herein included. The discussion is on a level which assumes the reader is familar with using window-type (mouse based) computing systems. In carrying out the procedure described below, it is helpful to include SimpleText, Photoshop, and Video Monitor in the Apple Control menu of the computer system. Also, the following procedure makes reference to various tools in the Photoshop toolbox. The reader should consult the Photoshop user manual or open the Photoshop application as a graphical aid in using the tools described below:

1. DISPLAY MICROSCOPE IMAGE OF DEVICE ON MONITOR

Position the device under the microscope to get the desired view and at the desired magnification. Transmit the magnified image to the computer monitor by selecting "Video Monitor" from the Apple Control menu. The desired device view is preferably centered on the monitor, is in focus, and occupies a substantial portion, if not all, of the monitor.

2. TAKE SNAPSHOT OF DEVICE IMAGE

The image on the monitor can be copied by pressing simultaneously pressing "⌘", (also referred to as the Command key) and "C". This is essentially the universal copy command in programs for the Macintosh. Copying the video image creates a PICT files of the image on the computer desktop.

3. OPEN PICT FILE FROM WITHIN PHOTOSHOP

Open Photoshop by selecting "Photoshop" from the Apple Control menu. Within Photoshop, choose "Open" from the "File" menu and select the PICT file copied to the desktop in Step 2.

4. SET PHOTOSHOP SETTINGS

Under the "Mode" menu, select "Indexed Color . . . ". Set the resolution to 8 bits/pixel. Set Palette to "System". Set Dither to "none." Click OK. This greatly enhances resolution of the PICT file image appearing on the monitor.

5. SET COLORS

In the Photoshop toolbox, set the "Foreground" and "Background" color boxes to black, or whatever color is desired for the opaque portions of the template to be created. To change the color, click on the Foreground box and enter the numerical red, blue, and green equivalents of the desired color (e.g. for black set R=0, B=0, and G=0). Do the same to change the Background color. For purposes of creating templates in accordance with this procedure, the Foreground and Background color are initially set to the same value.

6. ENLARGE IMAGE

Select the "Full Screen without menu bar" tool from the bottom right corner of the toolbox. This centers the PICT file image on the screen and frames it in a black background, blocking out extraneous images from the computer desktop. Then select the "Zoom" tool from the Photoshop toolbox. Move the cursor (which should now look like a magnifying glass) to anywhere on the PICT file image and click. This magnifies the PICT file image to the original size of the snapshot taken in Step 2, which should correspond in size to the image which is transmitted from the microscope to the monitor via the camera in Step 1.

7. CHANGE BACKGROUND TO TRANSPARENT

Next, the background color is made transparent. The user manual of Photoshop does not explain how to do this. Applicants discovered the Background in Photoshop can be changed to transparent as explained in the following two steps, although an understanding of why these steps make the Background transparent is not understood.

- a. While still in Photoshop and viewing the enlarged PICT file image created in Step 6, select "Video Monitor" from the Apple Control menu. This step displays a "live" image of the device under the microscope (hereinafter called the Video image), rather than the PICT file image.
- b. Now select "Photoshop" from the Apple Control menu. This step reverts the image being displayed on the monitor back to the PICT file image, but also (unexpectedly) changes the Background color box to be transparent. (In other words, what appears in the Background color box should be a portion of the Video image, which was the last "window" open on the monitor as created in step a. To check to see if this in fact is the case, lightly shake the stage of the microscope and see if the image appearing in the Background color box moves.)

The result of performing steps a and b is to have 3 different "layers" open at one time: on top is a PICT file image of the device under the microscope; next is a transparent background window (as opposed to a more conventional white or black background); and on bottom is the Video image of the device under the microscope.

8. PAINT AND ERASE PICT FILE IMAGE

The PICT file image should appear as the top layer of the 3-layer stack described in Step 7. The template will be created by painting and erasing this PICT file image as follows.

a. Select "Air Brush" from the Photoshop toolbox and paint over a portion of the image. The paint will be black, or whatever color was selected for the Foreground color. The only reason why the entire PICT file image is not painted over is to provide a frame of reference for how much of the paint to erase in step b.

b. Select "Eraser" from the Photoshop toolbox. Erase that portion of the paint created in step a to create the transparent portions of the template. Upon erasing the paint, the Background which is exposed is transparent, meaning that the underlying Video image is shown in the erased area, being visible through the transparent Background. (Again, to test that the image appearing in the erased area is the Video image, shake the microscope stage lightly and see if the image in the erased area moves).

c. Repeat steps a and b until the entire template is created.

The erased area should correspond to that area of the template to be transparent, while the remaining painted areas will form the opaque areas of the template. It is useful to paint and erase only parts of the template at one time (e.g. a third at a time) so that the unpainted portions of PICT file image can be used to approximate where the painted portions should be erased. However, since the Video image and the PICT file image are virtually identical, it is sometimes difficult to tell whether the area being looked at is part of the underlying Video image (being viewed through a transparent Background) or part of the PICT file image. When in doubt, lightly shake the microscope stage. The Video image should move. If an area is over-erased (too much has been erased) it's not a problem. The area can simply be repainted and erased again. Furthermore, the Line tool can be used in place of the Air Brush to paint more precisely.

9. ADD ALPHA-NUMERIC REFERENCES IF DESIRED

Alpha-numeric labels can be added to the template to aid in the inspection, for instance by having a wire bond count, or by indicating a non-standard type of wire bond. To add alpha-numerics to the template, select the "Type" tool from the Photoshop toolbox. Change the "Foreground Color" in the toolbox to a color which will show up on the opaque regions of the template. If the opaque regions are black, a text color of green (G=255, R=0, B=0) works well. Place the cursor where the label is to be located using the mouse, and type in the desired text.

10. SAVE TEMPLATE

Once the transparent and opaque regions and alphanumerics are satisfactorily established, save the template by choosing "Save" under the File menu, or simultaneously pressing "⌘" (also referred to as the Command key) and "S". Saving the template in Photoshop maintains the file format as a PICT file. Preferably the saved file is named to correspond to the particular device part number or type and inspection characteristic for which the template was created to inspect.

11. CONVERT PICT FILE TO TTXT FILE

In order for Simple Text to be able to read the template, the template must be converted from a PICT format to a readable format, such as ttxt. To convert the PICT template, quit the Photoshop application and return to the computer desktop. Drag the PICT template that was saved onto the File Typer application. Upon doing this, a "File Typer File Editor" window appears. In this window, type "ttxt" in the "Creator" box, then click the "Change" box. The template will now be saved as a ttxt file. Note that a conversion to ttxt format is not necessary if the system using the templates is capable of reading Photoshop's PICT files.

Once a template is created for the device type and characteristic that is being inspected, for example as explained in the above procedure, the template can be stored in the computer memory of a master system and remotely accessed from satellite systems. In practice, it is likely that multiple templates, one for each of the characteristics to be inspected and for each of the manufacturer's product type to be inspected, will be stored on the master system. As previously mentioned, one suitable embodiment for the master system includes consisting of the handling system (Allteq 3000) equipped with a microscope, a CCD camera (Sony Model No. SSC/C374), and a computer system with a monitor and a keyboard (Apple Computer Macintosh Quadra 840 AV). Suitable master system software includes Simple Text, File Typer, Quick Keys, and Photoshop. Each satellite system includes the same hardware. However, it is noted that while both the master system and satellite systems include microscopes, the microscopes on the two different systems need not be of the same caliber. For example, the satellite systems may require better microscopes to enable performance of other types of product inspection. For reasons explained below, it is not necessary that all master system software also be included on the satellite systems.

Preferably, the creation and storage of templates and the maintenance of the master system is controlled by the quality assurance group of the semiconductor manufacturer. Satellite stations then access the template information from the master system. In using a master-satellite combination, one computer system can be used to control access to the templates so that modifications or changes cannot be inadvertently made and that templates cannot be duplicated. Use of lesser equipped satellite systems no only insure tighter control of the templates used and created, but also are more cost effective since not all software used need be installed on the satellite systems. For example, templates created in Photoshop are initially saved as PICT files. The File Typer software can be used to convert the templates from PICT files, to ttxt files. With the templates in ttxt format, the Simple Text software of a satellite systems can read the templates, removing the need to install the Photoshop software on the satellite stations. In a preferred form, the satellite systems only have Simple Text and Quick Keys software in common with the master system.

At the satellite inspection stations, the operator preferably has options for selecting a particular template for the device being inspected. For example, one template may be for a 52 leaded plastic leaded chip carrier (PLCC) package, while another is for a 64 leaded plastic quad flat pack (PQFP) package. The operator needs to be able to select the appropriate template. But again, the operator at the satellite station should not have the ability to modify or delete the templates from the master system. Once the appropriate template is retrieved, and displayed, superimposed onto an image of the device being inspected, the inspector performs a comparison to see if the device is in compliance with quality standards.

The foregoing description and illustrations contained herein. demonstrate many of the advantages associated with the present invention. In particular, it has been revealed that a simple system using inexpensive hardware and software can be used to establish an inspection process for semiconductor manufacturers which has quick results. An inspection station operator need only to look at one image on a computer monitor to, determine if the device passes or fails the inspection process. Moreover, the image being viewed is simplified and only the characteristic that is being inspected is highlighted on the screen. The operators attention is focused on the particular area necessary for the inspection, while extraneous portions of the image of the device are blocked or hidden by a template. The superimposed image on the computer monitor provides a pass/reject answer to whether the device passes inspection. The present invention is easily incorporated into a manufacturing environment, is easily operated by an inspection station operator having even minimal computer experience, and is conducive to the manufacturer's goal of minimizing the time it takes to complete an inspection. Another advantage of using the present invention is that the device being inspected can be viewed in full field on the computer monitor, so that neither the device nor the inspection equipment need be moved or adjusted to allow inspection of the entire device.

Thus it is apparent that there has been provided in accordance with the present invention a method for inspecting a semiconductor device that fully meets the need and advantages set forth previously. Although the invention has been described and illustrated with reference to specific embodiments thereof, it is not intended that the invention be limited to these illustrative embodiments. Those skilled in the art will recognize that modifications and variations can be made without departing from the spirit of the invention. For example, the invention is not limited to inspecting wire bond configurations, die attach material bondline locations, or lead or mark postions of a semiconductor device. These particular inspection processes were described herein as examples of how the present invention can be implemented at a variety of inspection points throughout the manufacturing process. It is envisioned that other inspection stages will also benefit from the present invention. In addition, the invention is not limited to the specific hardware or software equipment described in the working example. The specific details described in the working example were only intended to enable one of ordinary skill in the art to readily practice the invention, but is not intended to limit the scope of the invention. For example, rather than employing a full microscope in conjunction with a camera to display a magnified image of the device being inspected on the monitor, a camera and magnification lens combination is sufficient. Furthermore, the template images need not be permanently stored in the computer's memory, but can instead be read or retrieved from a floppy disk or tape. It is also important to note that the specific template images illustrated herein are not the only template images which can be used in practicing the present invention. For example, the template can include various colors intended to designate a particular feature of the device, or may include a variety of alpha-numeric symbols to aid in the inspection process. Furthermore, it is not necessary that both a master system or station and a satellite station be used to practice the invention. Therefore, it is intended that the invention encompass all such variations and modifications to fall within the scope of the appencied claims.

I claim:

1. A method for inspecting a semiconductor device comprising the steps of:

providing a semiconductor device having a characteristic to be inspected;

providing an inspection station having a magnification lens, a monitor, and a camera coupled to the magnification lens and the monitor for transmitting magnified images created by the magnification lens to the monitor;

creating a template which represents an acceptable range of values for the characteristic;

storing the template in a computer readable memory;

placing the semiconductor device under the magnification lens;

displaying a magnified image of the semiconductor device on the monitor using the camera;

retrieving the template from the computer readable memory;

displaying an image of the template on the monitor, superimposed with the magnified image of the semiconductor device; and comparing the magnified image of the semiconductor device with the template to see if the characteristic of the semiconductor device falls within the acceptable range of values.

2. The method of claim 1 wherein the step of providing a semiconductor device comprises providing a semiconductor device having a die attach material bondline as the characteristic to be inspected.

3. The method of claim 2 wherein the step of displaying an image of the template comprises displaying at least two opaque lines that together define a lower limit and an upper limit for an acceptable location of the die attach material bondline along a side face of a semiconductor die.

4. The method of claim 1 wherein the step of providing a semiconductor device comprises providing a semiconductor device having a wire bond configuration as the characteristic to be inspected.

5. The method of claim 4 wherein the step of displaying an image of the template comprises displaying an image of a template which is transparent in regions corresponding to wire bonded areas and is opaque in other areas.

6. The method of claim 1 wherein the step of creating a template comprises creating a template having alpha-numeric notations to aid in the step of comparing.

7. The method of claim 1 wherein the step of providing a semiconductor device comprises providing a packaged semiconductor device having a plurality of leads, wherein the characteristic to be inspected is a location of each lead of the plurality of leads.

8. The method of claim 7 wherein the step of displaying an image of the template comprises displaying a transparent polygon corresponding in location within the template to an acceptable location for a lead to be inspected.

9. A method for inspecting a semiconductor device comprising the steps of:

provi ding an semiconductor die having a plurality of wire bonds;

providing a computer having a memory and having a monitor;

providing an inspection station having a handling system for moving the semiconductor die, a microscope for viewing the semiconductor die, and a camera coupled to the microscope and the monitor to portray a magnified image of the semiconductor die on the monitor;

using the handler to position the semiconductor die in a field of view of the microscope;

displaying the magnified image of the semiconductor die on the monitor;

retrieving a template of a wire bond configuration from the memory of the computer;

displaying an image of the template on the monitor, superimposed on the magnified image of the emiconductor die; and comparing the semiconductor die and the plurality of wire bonds to the template to see if the semiconductor die is properly wire bonded.

10. The method of claim 9 wherein the step of displaying an image of the template comprises displaying the image such that the image includes a graphical symbol indicating a desired wire bond count for a segment of the semiconductor die.

11. The method of claim 9 wherein the step of displaying a magnified image of the semiconductor die comprises displaying a magnified image of an entirety of a top surface of the semiconductor die.

12. The method of claim 9 wherein the step of displaying an image of the template comprises displaying the image such that the image is transparent in areas associated with the plurality of wire bonds and is opaque in other areas.

13. The method of claim 12 further comprising the step of toggling displays on the monitor between the magnified image of the semiconductor die and the image of the template superimposed on the magnified image of the semiconductor die to look for wire bonds which may be hidden by opaque areas of the image of the template.

14. A method of inspecting a semiconductor device comprising the steps of:

providing a semiconductor die having a plurality of bond pads formed on a surface;

providing a plurality of leads and a die flag;

mounting the semiconductor die to the die flag;

wire bonding a plurality of wire bonds between the plurality of bond pads and the plurality of leads to create a wire bonded die; and inspecting the plurality of wire bonds for accuracy of configuration, wherein the step of inspecting comprises the steps of:

positioning the wire bonded die on a stage within a field of view of a microscope;

transmitting a magnified image of the wire bonded die from the microscope to a monitor using a camera;

retrieving a template file from a computer readable memory;

using the template file to display an image of a wire bond template on the monitor superimposed onto the magnified image of the wire bonded die, wherein the image of the wire bond template has a transparent region outlining an area of the wire bonded die which is supposed to include at least one wire bond, and wherein the magnified image of the wire bonded die is visible on the monitor within the transparent region.

15. The method of claim 14 wherein the step of positioning comprises positioning the wire bonded die such that an entirety of the surface is within the field of view of the microscope.

16. The method of claim 14 wherein the step of using the template file comprises using the template file to display an image of a wire bond template, wherein the wire bond template has an opaque region corresponding to a region of the wire bonded die which is supposed to be void of any wire bonds, and wherein the magnified image of the wire bonded die cannot be seen on the monitor within the opaque region.

17. The method of claim 14 wherein the step of using the template file comprises using the template file to display an image of a wire bond template which includes alphanumeric symbols for aiding in the step of inspecting.

18. A method for inspecting a semiconductor device comprising the steps of:

providing a semiconductor die having a plurality of sides, each side having a height;

providing a substrate;

mounting the semiconductor die to the substrate using a die attach material, wherein the step of mounting creates a die attach material bondline along each side of the semiconductor die; and inspecting a location of the die attach material bondline, wherein the step of inspecting comprises the steps of:

positioning one side of the semiconductor die within a field of view of a microscope;

transmitting a magnified image of the one side from the microscope to a monitor;

retrieving a template file from a computer readable memory; and using the template file to display an image of a bondline template on the monitor, superimposed onto the magnified image of the one side of the semiconductor die, wherein the image of the bondline template has a transparent region appoximately corresponding in position and size to the one side as magnified and has a first opaque line corresponding to an acceptable location of the die attach material bondline, and wherein the magnified image of the one side is visible on the monitor within the transparent region.

19. The method of claim 18 wherein the step of using the termplate file comprises using the template file to display an image of a bondline template, wherein the image of the bondline template has a second opaque line, wherein the first opaque line corresponds to a maximum acceptable location of the die attach material bondline, and wherein the second opaque line corresponds to a minimum acceptable location of the die attach material bondline.

20. A method for inspecting a semiconductor device comprising the steps of:

providing a packaged semiconductor device having a plurality of external leads; and inspecting a position of each lead of the plurality of external leads, the step of inspecting comprising the steps of:

positioning the packaged semiconductor device within a field of view of a microscope such that all leads of the plurality of external leads are visible within the field of view;

transmitting a magnified image of the packaged semiconductor device from the microscope to a monitor;

retrieving a template file from a computer readable memory;

generating a template image from the template file, wherein the template image includes a transparent region defining a boundary of an acceptable, lead location; and displaying the template image on the monitor, superimposed on the magnified image of the packaged semiconductor device such that at least one lead is visible on the monitor through the transparent region.

21. The method of claim 20 wherein the step of generating a template image comprises generating a template image having a plurality of transparent regions, wherein each lead of the plurality of external leads has a corresponding transparent region.

22. The method of claim 21 wherein each transparent region of the plurality of transparent regions has a quadrangle shape.

* * * * *